United States Patent
Yu et al.

(10) Patent No.: US 9,797,771 B2
(45) Date of Patent: Oct. 24, 2017

(54) DIACETYLENE FILM SENSITIZED WITH PHOTOINITIATOR AND APPLICATIONS OF THE FILM

(71) Applicant: ISP INVESTMENTS INC., Wilmington, DE (US)

(72) Inventors: Xiang Yu, Bridgewater, NJ (US); Hsiao-Yi Shih, Whippany, NJ (US); David Lewis Fairhurst, Monroe, CT (US)

(73) Assignee: ISP INVESTMENTS INC., Wilmington, DE (US)

( * ) Notice: Subject to any disclaimer, the term of this patent is extended or adjusted under 35 U.S.C. 154(b) by 0 days.

(21) Appl. No.: 14/777,602

(22) PCT Filed: Mar. 7, 2014

(86) PCT No.: PCT/US2014/021777
§ 371 (c)(1),
(2) Date: Sep. 16, 2015

(87) PCT Pub. No.: WO2014/150000
PCT Pub. Date: Sep. 25, 2014

(65) Prior Publication Data
US 2016/0290859 A1   Oct. 6, 2016

Related U.S. Application Data

(60) Provisional application No. 61/803,831, filed on Mar. 21, 2013.

(51) Int. Cl.
*G01J 1/42* (2006.01)
*G03C 1/73* (2006.01)
(Continued)

(52) U.S. Cl.
CPC ............... *G01J 1/429* (2013.01); *C08J 7/047* (2013.01); *C09D 4/00* (2013.01); *C09D 5/32* (2013.01);
(Continued)

(58) Field of Classification Search
CPC .............. G01J 1/429; C08J 7/047; C09D 4/00
See application file for complete search history.

(56) References Cited

U.S. PATENT DOCUMENTS

| | | |
|---|---|---|
| 3,836,368 A | 9/1974 | Jun et al. |
| 5,420,000 A | 5/1995 | Patel et al. |

(Continued)

OTHER PUBLICATIONS

International Search Report, PCT/US2014/021777 published on Sep. 25, 2014.

*Primary Examiner* — David Porta
*Assistant Examiner* — Mindy Vu
(74) *Attorney, Agent, or Firm* — William J. Davis

(57) ABSTRACT

A process for improving sensitivity of a film base, coated with a dispersion of a normally crystalline polyacetylenic compound in a non-solvating liquid which is dried on the film surface, to particular photon energy band, specifically, long wavelength UV; the polyacetylenic compound preferably having at least two conjugated acetylenic linkages and containing from 12 to 60 carbon atoms. The sensitization of the film to long wavelength UV is achieved via the addition of photoinitiator(s) capable of absorbing UV energy and converting it to free radicals.

5 Claims, 2 Drawing Sheets

(51) Int. Cl.
*C08J 7/04* (2006.01)
*C09D 4/00* (2006.01)
*C09D 5/32* (2006.01)
*G01N 33/49* (2006.01)

(52) U.S. Cl.
CPC ............... *G01N 33/49* (2013.01); *G03C 1/73* (2013.01); *C08J 2367/00* (2013.01); *C08J 2429/04* (2013.01); *C08J 2449/00* (2013.01)

(56) References Cited

U.S. PATENT DOCUMENTS

2003/0129759 A1* 7/2003 Lewis ..................... G01T 1/06
  436/58
2010/0247899 A1  9/2010 Shih et al.

* cited by examiner

DIACETYLENE FILM SENSITIZED WITH PHOTOINITIATOR AND APPLICATIONS OF THE FILM

FIELD OF THE INVENTION

This invention relates to a film that is specifically manufactured for measuring long wavelength Ultraviolet (UVA) light. More specifically, it relates to a film manufactured for use in indicating an exposure and/or measuring dose of the exposure of long wavelength UV that is commonly used for UV curing of coating, pathogen inactivation and other industrial and medical applications.

BACKGROUND OF THE INVENTION

UV curing is a photochemical process in which high-intensity ultraviolet light is used to instantly cure or "dry" inks, coatings or adhesives. Since its introduction, UV curing has been widely adopted in many industries including automotive, telecommunications, electronics, graphic arts, converting and metal, glass and plastic decorating. Popularity of UV curing has been increasing steadily owing to its many advantages over traditional drying methods.

Using light instead of heat, the UV curing process is based on a photochemical reaction. Liquid monomers and oligomers are mixed with a small percent of photoinitiators, and then exposed to UV energy. In a few seconds, the products—inks, coatings or adhesives instantly harden.

In recent years, pathogen reduction using riboflavin and UV light has been developed to inactivate infectious pathogens in blood ready for transfusion. This method reduces the infectious levels of disease-causing agents that may be found in donated blood components, while still maintaining good quality blood components for transfusion.

The development of pathogen inactivation/reduction technologies for blood products has been an ongoing effort in the field of transfusion medicine. The riboflavin and UV light method for pathogen reduction of platelets and plasma has been accepted in many countries throughout Europe. This same process is currently in development for the treatment of whole blood, resulting in pathogen reduction of the three components (RBCs, platelets and plasma). The application in United States and other countries will follow soon with regulatory issues being resolved.

In the applications listed above, precise control of UV illumination dose can be critical. A simple color change film indicating an exposure and/or measuring dose of the exposure of long wavelength UV can be very useful.

Lewis et al. (U.S. Pat. No. 4,734,355 and U.S. Pat. No. 4,970,137) have disclosed a type of radiochromic film which is sensitive to ionizing radiation. Upon radiation, a crystalline diacetylene undergoes solid state polymerization and forms colored polymer from colorless monomers. This type of film is particular sensitive to short wavelength UV, known as UVC with wavelength between 200 and 280 nm. The particular film is found to be less sensitive to the radiation of UV of long wavelength between 280 and 400 nm.

It is the objective of this invention to develop a film that has sensitivity to long wavelength UV to the extent required by the particular applications.

It is further the objective of this invention to develop a long wavelength UV indicator and/or dosimeter based on the film that indicates an exposure and/or measuring dose of long wavelength UV.

SUMMARY OF THE INVENTION

A film media is hereby disclosed which is sensitive to long wavelength UV and is suitable for use for measuring exposures within the range from about 0.01 to 20 $J/cm^2$.

Furthermore, the film of the present invention provides a UV sensitive media that is particularly sensitive to UVA with wavelength from 280 to 400 nm that are most commonly used in the said applications.

In addition, the present invention provides a film media that can be easily manufactured with existing coating techniques and the resulting film products can be easily converted into different forms with commonly available web handling techniques.

More particularly, we have developed a film media which is sensitive to long wavelength UV from 280 to 400 nm which is composed of a first support layer of a polymeric film which is transparent for long wavelength UV and a second layer thereon of a composition comprising a dispersion of a substantially crystalline polyacetylenic compound, and a photoinitiator or mixture of photoinitiators that are capable of adsorbing long wavelength UV and generating free radicals for initiation of polymerization of the said crystalline polyacetylenic compound.

Furthermore, we have developed applications for such UV sensitive films for example, the films can be utilized to indicate whether an exposure has occurred and/or used for quantitatively measuring the dose of the exposure.

BRIEF DESCRIPTION OF THE FIGURES

Further embodiments of the present invention can be understood with the appended figures.

DETAILED DESCRIPTION OF THE INVENTION

Figure 1:
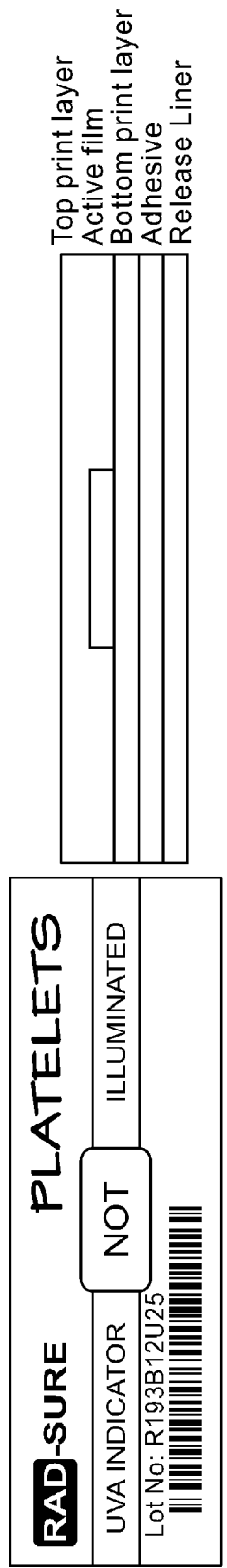
FIG. 1 is a UVA Indicator

While this specification concludes with claims particularly pointing out and distinctly claiming that which is regarded as the invention, it is anticipated that the invention can be more readily understood through reading the following detailed description of the invention and study of the included examples.

The singular forms "a," "an," and "the" include plural forms unless the context clearly dictates otherwise specified or clearly implied to the contrary by the context in which the reference is made. The term "comprising" is an open-ended claim encompasses the closed-ended terms such as "consisting", "consisting of" and "consisting essentially of".

All references to singular characteristics or limitations of the present invention shall include the corresponding plural characteristic or limitation, and vice-versa, unless otherwise specified or clearly implied to the contrary by the context in which the reference is made.

The term "about" can indicate a difference of 10 percent of the value specified. Numerical ranges as used herein are meant to include every number and subset of numbers enclosed within that range, whether particularly disclosed or not. Further, these numerical ranges should be construed as providing support for a claim directed to any number or subset of numbers in that range.

As used herein, the words "preferred," "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

References herein to "one embodiment", "one aspect" or "one version" or "one objective" of the invention include one or more such embodiment, aspect, version or objective, unless the context clearly dictates otherwise.

All publications, articles, papers, patents, patent publications, and other references cited herein are hereby incorporated herein in their entireties for all purposes to the extent consistent with the disclosure herein.

Suitable acetylenic compounds for use in the present invention are represented by the structure:

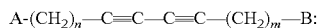

$$A\text{-}(CH_2)_n\text{—}C\equiv C\text{—}C\equiv C\text{—}(CH_2)_m\text{—}B:$$

wherein m and n are both independently an integer of from about 0 to 20 and A and B are independently methyl or carboxyl groups.

Specific examples of such polyacetylenes include pentacosa-10,12-diynoic acid; 13,15-octacosadiyne and docosa-10,12-diyne-1, 22-dioic acid. Of these, pentacosa-10,12-diynoic acid is most preferred since it provides unusually high sensitivity to ionizing radiation exposure. It is to be understood however, that dispersions of other normally crystalline, color developing polyacetylenes having a conjugated structure can be employed alone or in admixture with the preferred diynes as the image receptive layers of the present invention. Such compounds include the diynes of the above structure wherein the A and/or B moieties, in addition to lower alkyl or carboxyl, can also be hydroxy, amido, lower alkyl substituted amido, an aliphatic or aromatic carboxylate ester group having up to 10 carbon atoms, a mono- or di-valent carboxylate metal salt group, halo, carbamyl, lower alkyl substituted carbamyl or tosyl, as well as the corresponding triyne and tetrayne products of the above polyacetylenes having from 20 to 60 carbon atoms and a conjugated structure. Examples of these compounds include 10,12-docosadiynediol, the ditoluene-p-sulfonate of 9,11-eicosadiynoic acid, the monoethyl ester of 10,12-docosadiynedioic acid, the sodium or potassium salt of 10,12-pentacosadiynoic acid, the zinc salt of heneicosa-10,12-diynoic acid, the manganese salt of eicosa-5,7-diynoic acid, 10,12-docosadiyne chloride, 10,12-pentacosadiyne (m-tolyl-urethane), 10,12-pentacosadiyne {[(butoxyl-carbonyl)-methyl]urethane}, N-(dimethyl)-10,12-pentaco sadiynamide, N,N-bis-(α-methylbenzy-1)-10,12-pentacosadiyndiamide and the like. In addition, the polyacetylenic compounds for use in accordance with the invention generally may also have the formulae:

$$R\text{—}C\equiv C\text{—}C\equiv C\text{—}R'$$

wherein R and R' are, for example, both $CH_2\text{—}O\text{—}CONH\text{—}(CH_2)_5CH_3$.

Such polyacetylenic compounds polymerize in the solid state either upon thermal annealing or exposure to high energy radiation. Suitable compounds are described in U.S. Pat. No. 5,420,000, U.S. Pat. No. 4,970,137, and U.S. Pat. No. 4,734,355, the contents of each of which are incorporated herein by reference. Preferably, the polyacetylenic compound has at least two conjugated acetylenic linkages and contains from about 10 to 60 carbon atoms.

Suitable photoinitiator is a compound especially added to the formulation to convert absorbed light energy, UV or visible light, into chemical energy in the form of initiating species, viz., free radicals or cations. In the invention disclosed here, the photoinitiator selectively absorbs incident UV photon radiation and generates free radical to initiate the polymerization of the above mentioned crystalline polyacetylenic compounds. Based on the mechanism by which initiating radicals are formed, photoinitiators are generally divided into two classes:

Type I photoinitiators undergo a unimolecular bond cleavage upon irradiation to yield free radicals.

Type II photoinitiators undergo a bimolecular reaction where the excited state of the photoinitiator interacts with a second molecule (a co-initiator) to generate free radicals.

These photoinitiators may be added generally in an amount of from about 0.01% to 10.0%, and preferably 0.05% to 1% by weight of the dispersion of the coating as described hereinafter.

Most preferably, suitable photoinitiators include benzoin, benzil derivatives, ketal derivatives, alkyl phenones, acylphosphine oxide, halogenated methyl ketones, thioxanthone and xanthone. Those photoinitiators are commonly available from major chemical manufacturers.

In preparing the film, the polyacetylenic compound is dispersed in a non-solvating liquid such as water. This dispersion also contains a dissolved polymeric binder. Examples of binders include, but are not limited to, gelatin, agar, xanthan gum and polymers and copolymers containing vinyl alcohol, maleic acid or acrylic acid residues, or salts thereof. The liquid dispersion is then applied onto the surface of a film, e.g., a polyester or similar film, and the coating is then dried. In particular, the normally crystalline polyacetylenic compound is dispersed into the non-solvating liquid in a concentration of from about 2 to 50% based on the combined weights of the polyacetylenic crystalline compound, the non-solvating liquid and the polymeric binder dissolved therein.

In accordance with the present invention, a photoinitiator or combination of photoinitiators is mixed with the polyacetylenic containing dispersion in an amount which is effective to absorb incident long wavelength UV photon radiation when the dried composition is exposed thereto.

The thus mixed composition is then applied as a layer onto a substrate or support layer which is a polymeric film transparent to long wavelength UV. The thus coated substrate is then dried at a temperature from about ambient up to about 100° C., but below the distortion temperature of the substrate and below the decomposition temperature of any of the components of the coating or the melting point of the polyacetylene compound therein.

The film thus formed is sensitive to radiation and especially to that of long wavelength UV. Upon irradiation, a polymerization process is initiated in the polyacetylenic compound resulting in an immediate change in the color of the coating. The color darkens in proportion to the radiation exposure. The degree of darkening may be measured with a number of instruments including densitometers, spectrophotometers and film scanners.

Since the film darkens in proportion to radiation exposure, it is possible to measure the darkening and use this measurement as a means for determining the amount of the radiation exposure. Thus, the film may be employed as a radiation dosimeter, to measure and map radiation fields.

Further, certain aspects of the present invention are illustrated in detail by way of the following examples. The examples are given herein for illustration of the invention and are not intended to be limiting thereof.

Example 1: Radiation Sensitive Dispersion

A microcrystalline dispersion of lithium salt of pentacosa-10,12-diynoic acid in aqueous polyvinyl alcohol solution was prepared by procedures similar to those disclosed in U.S. Pat. No. 7,445,880.

Example 2: Formulation of Radiochromic Coating Fluid

A typical radiochromic fluid is shown in Table 1.

TABLE 1

A typical composition of radiochromic fluid

| Ingredients | Percentage (%) |
| --- | --- |
| Active polyacetylenic compound | 2-15 |
| Binder (polyvinyl alcohol) | 2-30 |
| Additives (surfactant, stabilizer and etc.) | 0.1-2 |
| Water | 45-95 |

Example 3: Aqueous Emulsion/Dispersion of Photoinitiators

Most photoinitiators have very limited water solubility. One way to formulate the photoinitiators into an aqueous based coating fluid with formulation as illustrated in Table 2 is to first disperse or emulsify the photoinitiator in water.

TABLE 2

A Composition of photoinitiator dispersion

| Ingredients | Percentage (%) |
| --- | --- |
| Photoinitiators | 1-20 |
| Solvent | 1-20 |
| Other Additives (Surfactant, stabilizer and etc.) | 0.1-3 |
| Water | 45-98 |

A finely dispersed photoinitiator emulsion or dispersion will have a milk white appearance and does not phase separate in the time period required to prepare a fluid for coating and apply it to a substrate.

Example 4: Evaluation of Photoinitiators

A radiochromic fluid formulation as shown in Table 3 was used for the evaluation of the effectiveness of the different photoinitiators in boosting the UVA sensitivity of the films prepared there from.

TABLE 3

Composition of Radiochromic Fluid

| Ingredients | Percentage (%) |
| --- | --- |
| Active | 8.0 |
| Binder (polyvinyl alcohol) | 10.0 |
| Additives (surfactant, stabilizer and etc.) | 1.0 |
| Water | 80.0 |
| Photoinitiators | 1.0 |

Example 5: Effect of Photoinitiators

Three different photoinitiators were added into fluids exemplified by Example 3 at concentration of the photoinitiator of 1%. Fluids were coated onto polyester substrate and dried. The resulting films as well as film obtained from with the fluid described in Example 1 were illuminated with a UV lamp of predominant long wavelength 320 to 400 nm to and exposure of 2.5 J/cm$^2$. The net optical density changes of the film as the results of UVA illumination and calculated boost of UVA sensitivities are shown in Table 4.

TABLE 4

Effect of photoinitiators

| Example | Photoinitiator | Film density change* | Sensitivity Boost** |
| --- | --- | --- | --- |
| A | none | 0.11 | 1 |
| B | Sodium salt of anthraquinone-2-sulfonic acid | 1.1 | 10 |
| C | 2-Methyl-1-[4-(methylthio)phenyl]-2-(4-morpholinyl)-1-propanone | 0.8 | 7.2 |
| D | 2-Hydroxy-2-methylpropiophenone | 0.95 | 8.65 |

*Net density change of the film with 2.5 J/cm$^2$ of UVA illumination
**Calculated based on the relative change as multiple of example A Example 6: Effect of Concentration of Photoinitiator Four different fluids were made by adding various concentrations of 2-Hydroxy-2-methylpropiophenone purchased from Aldrich. Fluids were coated onto polyester substrate and the resulting films together with film derived from the fluid in Example 1 were illuminated with a UV lamp of predominant long wavelength 320 to 400 nm at an exposure of 2.5 J/cm$^2$. The net optical density changes of the film as the result of UVA illumination and the calculated boost of UVA sensitivities are shown in Table 5. It is clear that over the experimental concentration range, the sensitivity boost is increased proportional to the photoinitiator addition.

TABLE 5

Effect of photoinitiator concentration on radiochromic film sensitivities to UVA

| Example | Photoinitiator concentration (%) | Film density change* | Sensitivity Boost** |
| --- | --- | --- | --- |
| A | 0 | 0.11 | 1 |
| E | 0.2 | 0.412 | 3.75 |
| F | 0.5 | 0.63 | 5.7 |
| G | 1 | 1.1 | 10 |
| H | 2 | 1.95 | 17.7 |

*Net density change of the film with 2.5 J/cm$^2$ of UVA illumination
**Calculated based on the relative change as multiple of example 1

Example 7: Stability of Photoinitiator Sensitized Film

Samples E, F, F, and H described in Example 6 were separately placed into black envelopes and stored in an (1) oven at 40° C., (2) in a refrigerator at between 2-4° C., and (3) at room temperature between 20-24° C. The optical transmission densities of the samples were re-measured after 1, 3, 7, 14 and 28 days.

The results for Samples E to F demonstrate that the film is exceptionally stable under storage in the dark, even at temperatures of 40° C. and 50° C. This means that the shelf life of film has no strong dependence on storage temperature and indicates that the film could be stored for long periods of time without significant change.

Example 8: Preparation of UVA Indicators Using Photoinitiator Sensitized Films

Using film obtained from Example 6 Samples E-H and the method disclosed by Lewis et. al. in U.S. Pat. No. 5,084,623, a UVA indicator were developed for UVA Blood Pathogen Inactivation System. As shown in FIG. 1, the active film is placed behind the window of a top printed layer and on top of bottom printed layer. The indicator as shown in FIG. 1 was then placed on a blood bag and subjected to illumination of 2.5 J/cm$^2$ of UVA.

Figure 2:
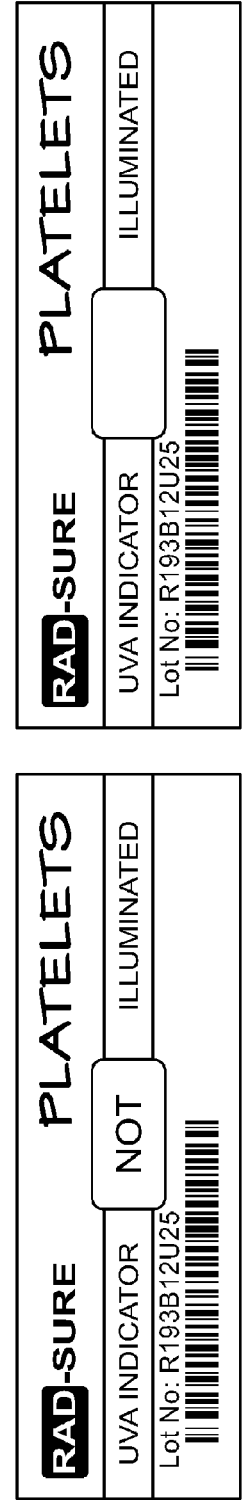
FIG. 2 shows a UVA Indicator before (left) and after (right) illumination of 2.5 $J/cm^2$ UVA FIG. 3 describes a sample calibration curve of a UVA dosimeter

As shown in FIG. 2, the distinct change in the indicator provides striking visual verification for the operator and an assurance that a particular unit to which the indicator is attached has received an UVA exposure. When a UVA indicator as illustrated is attached to a blood product and irradiated, the condition of the indicator signifies whether the product has been exposed to the requisite 2.5 J/cm$^2$ UVA to inactivate pathogens in the blood product and can be used for transfusion to a patient.

Example 9: UVA Dosimetry Film

Pieces of film exemplified by Sample E of Example 6 were illuminated with UVA from the same light source for different times and the changes in optical transmission density were measured using X-Rite 310T densitometer. The net density changes of the samples are shown in Table 6.

TABLE 6

| Optical Density of Sample F as function of UVA radiation dose | | |
|---|---|---|
| UVA Radiation Dose, J/cm$^2$ | Optical Density | Net Optical Density Change |
| 0.0 | 0.050 | 0.00 |
| 0.2 | 0.205 | 0.155 |
| 0.5 | 0.356 | 0.306 |
| 1.0 | 0.598 | 0.548 |
| 2.5 | 1.025 | 0.975 |
| 5.0 | 1.354 | 1.304 |

Figure 3:
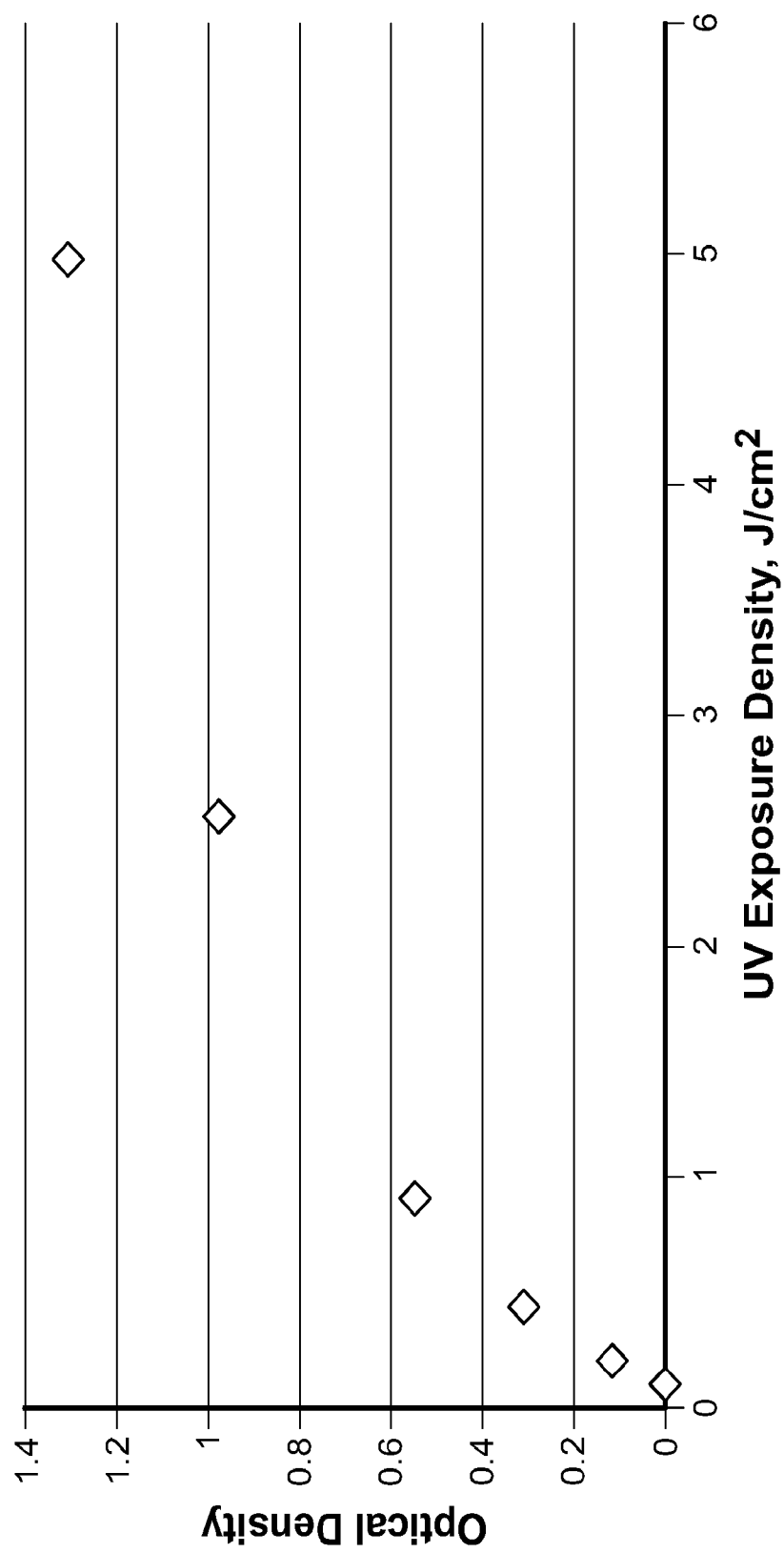

When the data in Table 6 were plotted as shown in FIG. 3, the density-dose correlation of the calibration curve can be easily established. Using said calibration curve, one can easily determine the UVA illumination dose by measuring the film density change.

While this invention has been described in detail with reference to certain preferred embodiments, examples and explanations set forth herein are provided for illustrative purposes only, it should be appreciated that the present invention is not limited to those precise embodiments, examples and explanations. Rather, in view of the present disclosure, various modifications and variations would present themselves to those skilled in the art without departing from the scope and spirit of this application and scope of the appended claims.

We claim:

1. A film media sensitive to long wavelength UV comprising a first support layer of polymeric film which is permeable to said UV and a second layer prepared from a radiochromic active fluid comprising a microcrystalline dispersion of a substantially crystalline image receptive polyacetylenic compound and a photoinitiator compound or mixture of photoinitiators, wherein said photoinitiator compound(s) are selected from the group consisting of sodium salt of anthraquinone-2-sulfonic acid, 2-methyl-1-[4-(methylthio)phenyl]-2-(4-morpholinyl)-1-propanone and 2-hydroxy-2-methylpropiophenone.

2. The film media of claim 1, wherein the polyacetylenic compound has the following structure:

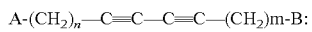

wherein m and n are both independently an integer from 6 to 14 and A and B are independent from one another and are selected from the group consisting of methyl, carboxyl, hydroxy, amido, lower alkyl substituted amido, aliphatic or aromatic carboxylate ester group having up to 10 carbon atoms, mono- or di-valent carboxylate metal salt group, halo, carbamyl, lower alkyl substituted carbamyl or tosyl, triyn or tetrayne products of the above polyacetylenes having from 20 to 60 carbon atoms and a conjugated structure, and combinations thereof.

3. The film media of claim 1, wherein the photoinitiator compound is present in an amount from about 0.01 to 10.0% by weight of the radiochromic active fluid.

4. The film media of claim 1, wherein the long wavelength UV has wavelength in the range between 280 to 400 nm.

5. The film media of claim 1, wherein the photoinitiator is present in an amount from about 0.05 to 1.0% by weight of the radiochromic active fluid.

* * * * *